United States Patent [19]

Sturm et al.

[11] Patent Number: 4,753,940
[45] Date of Patent: Jun. 28, 1988

[54] BARBITURIC ACID DERIVATIVES

[75] Inventors: Elmar Sturm, Aesch; Jean J. Gallay, Magden, both of Switzerland; Georg Pissiotas, Lörrach, Fed. Rep. of Germany

[73] Assignee: Ciba-Geigy Corporation, Ardsley, N.Y.

[21] Appl. No.: 827,118

[22] Filed: Feb. 7, 1986

[30] Foreign Application Priority Data

Feb. 15, 1985 [CH]  Switzerland ................... 704/85

[51] Int. Cl.$^4$ ................. A61K 31/495; C07D 253/04; C07D 403/10
[52] U.S. Cl. ..................... 514/252; 514/241; 514/242; 514/243; 514/248; 514/249; 514/253; 544/182; 544/183; 544/194; 544/209; 544/235; 544/239; 544/240; 544/241; 544/284; 544/296; 544/299; 544/300
[58] Field of Search ............... 544/182, 183, 194, 209, 544/235, 239, 240, 241, 284, 296, 299, 300, 295; 514/248, 249, 252, 253, 241, 242, 243

[56]  References Cited

U.S. PATENT DOCUMENTS 4,229,454  10/1980  Beriger ........................... 514/270
4,283,444   8/1981  de Sousa et al. ................ 514/155

FOREIGN PATENT DOCUMENTS 167491   1/1986  European Pat. Off. ............ 544/300
1499850  2/1978  United Kingdom .

OTHER PUBLICATIONS de Sousa et al., JSDC vol. 99 (1983) p. 118-121.

*Primary Examiner*—Donald G. Daus
*Assistant Examiner*—Cecilia Shen
*Attorney, Agent, or Firm*—Edward McC. Roberts; Meredith C. Findlay

[57]  ABSTRACT

The invention relates to novel phenylcarbamoylbarbituric acid derivatives of the general formula

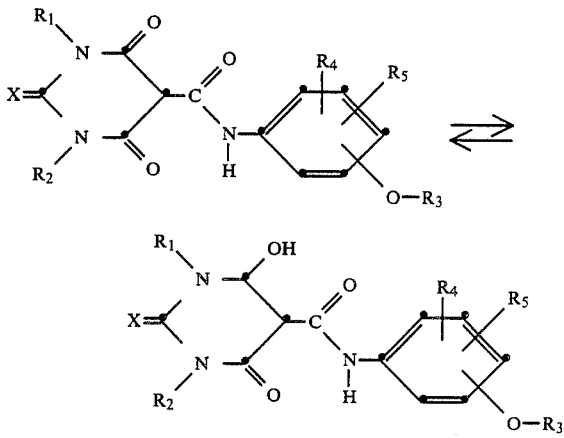

wherein
$R_1$ is $C_1$-$C_4$alkyl, $C_1$-$C_3$alkoxy, allyl or $C_3$-$C_6$cycloalkyl,
$R_2$ is $C_1$-$C_4$alkyl or allyl,
$R_3$ is an unsubstituted or substituted heteroaromatic 6-membered ring which contains 2 or 3 nitrogen atoms, or is an unsubstituted or substituted heteroaromatic 6-membered ring which is fused to a benzene ring and which contains 1 to 3 nitrogen atoms,
$R_4$ and $R_5$ are each independently of the other hydrogen, $C_1$-$C_4$alkyl, $C_1$-$C_4$alkoxy or $C_1$-$C_3$haloalkyl and
X is an oxygen or sulfur atom,
and to the tautomers and salts thereof.

These compounds may be used for controlling helminths which are parasites of animals.

15 Claims, No Drawings

BARBITURIC ACID DERIVATIVES

The present invention relates to novel substituted 5-phenylcarbamoylbarbituric acid derivatives having anthelmintic activity, to compositions containing these compounds as active ingredients, and to the use of said compounds or compositions for controlling helminths, in particular nematodes, cestodes and trematodes in domestic animals and productive livestock, especially in warm-blooded animals, in particular in mammals.

The invention further relates to the preparation of the novel compounds and of compositions containing them and to novel intermediates and to the preparation thereof.

Specifically, the invention relates to novel compounds of the general formula I

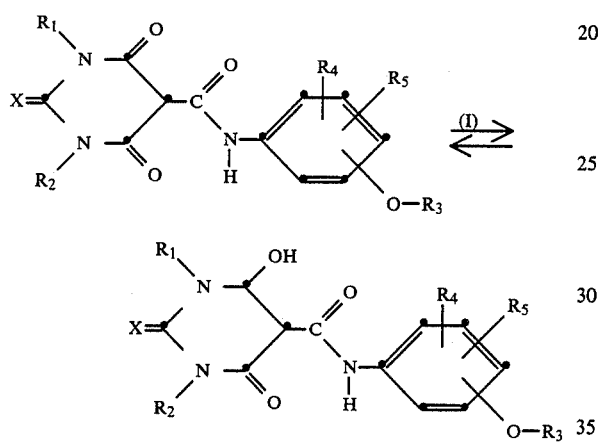

wherein
- $R_1$ is $C_1$–$C_4$alkyl, $C_1$–$C_3$alkoxy, allyl or $C_3$–$C_6$cycloalkyl,
- $R_2$ is $C_1$–$C_4$alkyl or allyl,
- $R_3$ is an unsubstituted or substituted heteroaromatic 6-membered ring which contains 2 or 3 nitrogen atoms, or is an unsubstituted or substituted heteroaromatic 6-membered ring which is fused to a benzene ring and which contains 1 to 3 nitrogen atoms,
- $R_4$ and $R_5$ are each independently of the other hydrogen, $C_1$–$C_4$alkyl, $C_1$–$C_4$alkoxy or $C_1$–$C_3$haloalkyl and
- X is an oxygen or sulfur atom, and to the tautomers and salts thereof.

The present invention also relates to the N oxides of compounds of formula I.

Examples of substituents $R_3$ are unsubstituted or substituted representatives selected from the group consisting of pyrimidinyl, triazinyl, pyrazinyl, pyridazinyl, quinolyl, isoquinolyl, phthalazinyl, quinoxalyl, quinazolinyl, cinnolinyl and benzotriazinyl.

Examples of possible substituents of the above-mentioned rings and ring systems are $C_1$–$C_4$alkyl, $C_1$–$C_4$haloalkyl, alkoxyalkyl containing a total of 2 to 4 carbon atoms, $C_1$–$C_4$alkoxy, $C_1$–$C_4$haloalkoxy, $C_1$–$C_4$alkylthio, $C_1$–$C_4$haloalkylthio, $C_1$–$C_3$alkylamino, di($C_1$–$C_3$alkyl)amino, allyl, propargyl, halogen, nitro, cyano, $C_3$–$C_6$cycloalkyl or phenyl.

$R_3$ is for example one of the following cyclic radicals:

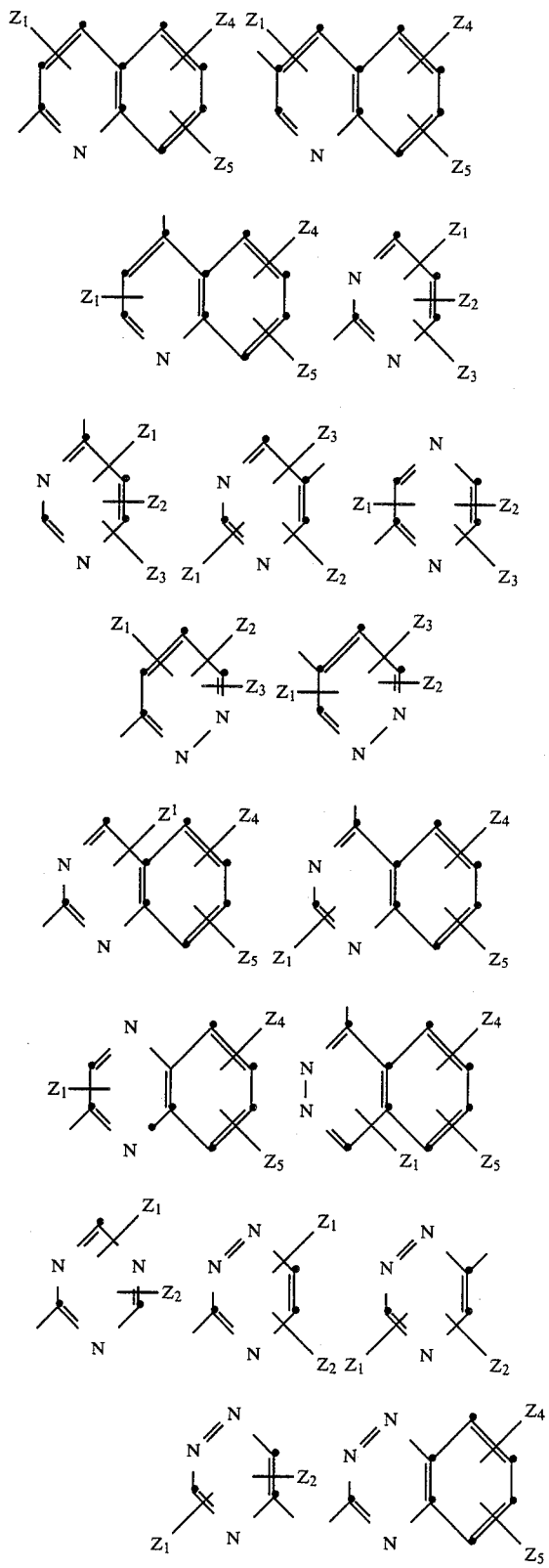

In the above radicals, each of $Z_1$, $Z_2$, $Z_3$, $Z_4$ and $Z_5$ independently of one another is hydrogen, $C_1$–$C_4$alkyl, $C_1$–$C_4$haloalkyl, alkoxyalkyl containing a total of 2 to 4 carbon atoms, $C_1$–$C_4$alkoxy, $C_1$–$C_4$haloalkoxy, $C_1$–$C_4$alkylthio, $C_1$–$C_4$haloalkylthio, $C_1$–$C_3$alkylamino, di(C-

$_1$-C$_3$alkyl)amino, allyl, propargyl, halogen, nitro, cyano, C$_3$-C$_6$cycloalkyl or phenyl, Z$_1$, Z$_2$ and Z$_3$ being on the heteroaromatic ring, and Z$_4$ and Z$_5$ being on the fused homoaromatic ring. Radicals Z$_1$, Z$_2$, Z$_3$, Z$_4$ and Z$_5$ to be singled out for particular mention are halogen, preferably chlorine, as well as trifluoromethyl and methylthio.

Alkyl as substituent or as moiety of a substituent shall be understood as meaning methyl, ethyl, n-propyl, isopropyl, n-butyl, isobutyl, sec-butyl and tert-butyl. These radicals are referred to collectively as lower alkyl.

Cycloalkyl is cyclopropyl, cyclobutyl, cyclopentyl and cyclohexyl, with cyclopropyl being preferred.

Halogen as substituent or as moiety of a substituent shall be understood as meaning fluorine, chlorine, bromine or iodine, with fluorine and chlorine being preferred and chlorine being most preferred.

Haloalkyl radicals are methyl containing 1 to 3 halogen atoms, e.g. chloromethyl and fluoromethyl, and C$_2$-C$_5$alkyl containing 1 to 5 halogen atoms. Alkyl radicals containing 3 halogen atoms are preferred.

Examples of C$_1$-C$_4$alkoxy are methoxy, ethoxy, n-propoxy, isopropoxy; examples of C$_1$-C$_4$alkylthio are methylthio and n-propylthio; examples of C$_1$-C$_4$haloalkoxy are chloromethoxy, fluoromethoxy, 2-chloroethoxy, 2,2-dichloroethoxy, 3-fluoro-n-propoxy and 2,2,2-trifluoroethoxy; and examples of C$_1$-C$_4$haloalkylthio are fluoromethylthio, chloromethylthio, 1,2-dichloroethylthio and 2,2-difluoromethylthio.

Within the scope of the present invention, a di(C$_1$-C$_3$alkyl)amino group shall be understood as being an amino group in which the two hydrogen atoms are replaced by two identical or different C$_1$-C$_3$alkyl groups. The dimethylamino group is preferred.

The salts of compounds of formula I comprise for example the alkali metal salts, ammonium salts or amine salts, with the sodium, potassium, ammonium or alkylamine salts being preferred. Preferred alkylamine salts are triethylamine salts.

Compounds of formula I of particular interest are those wherein R$_1$ is C$_1$-C$_4$alkyl, C$_1$-C$_3$alkoxy or C$_3$-C$_6$cycloalkyl and R$_2$ is C$_1$-C$_4$alkyl, and especially those wherein R$_1$ is methyl or methoxy and R$_2$ is methyl.

An interesting group comprises those compounds of formula I, wherein R$_1$ is C$_1$-C$_4$alkyl, preferably methyl or ethyl, methoxy, allyl or cyclopropyl, R$_2$ is methyl, R$_3$ is a pyrazinyl, pyridazinyl, triazinyl, pyrimidinyl, quinoxalinyl, quinolyl or quinazolinyl radical, each of which is unsubstituted or substituted by one to three substituents selected from the group consisting of C$_1$-C$_4$alkyl, preferably methyl, isopropyl and tert-butyl, methoxy, methylamino, dimethylamino, methylthio, trifluoromethyl, halogen, preferably chlorine, and phenyl, R$_4$ is hydrogen, C$_1$-C$_4$alkyl, preferably methyl or isopropyl, or methoxy, R$_5$ is hydrogen or methyl and X is an oxygen or sulfur atom.

Compounds of formula I also to be singled out for special mention are those in which the structural element —OR$_3$ on the phenyl ring is in the meta- or para-position, preferably in the para-position, to the carbamoyl radical of the barbituric acid.

A group meriting particular mention comprises compounds of formula I, wherein R$_1$ and R$_2$ are methyl, R$_3$ is a pyrazinyl, pyrimidinyl, pyridazinyl, quinoxalinyl or quinolyl radical, each of which is unsubstituted or substituted by one or two substituents selected from the group consisting of methyl, isopropyl, methoxy and chlorine, R$_4$ and R$_5$ are hydrogen and X is an oxygen or sulfur atom.

Of outstanding interest are the following groups (a) to (f) which are in increasing order of significance with regard to the effectiveness of the compounds comprised therein.

(a) Compounds wherein R$_1$ is C$_1$-C$_4$alkyl, C$_1$-C$_3$alkoxy, allyl or C$_3$-C$_6$cycloalkyl, R$_2$ is C$_1$-C$_4$alkyl, R$_3$ is a pyrazinyl, pyrimidinyl, pyridazinyl, triazinyl, quinoxalinyl or quinolinyl radical, each of which is bound through a carbon atom and is unsubstituted or substituted by one to three substituents selected from the group consisting of C$_1$-C$_4$alkyl, C$_1$-C$_4$haloalkyl, C$_1$-C$_4$alkoxy, C$_1$-C$_4$haloalkoxy, C$_1$-C$_4$alkylthio, C$_1$-C$_3$alkylamino, di(C$_1$-C$_3$alkyl)amino, allyl, halogen, C$_3$-C$_6$cycloalkyl and phenyl, R$_4$ is hydrogen, C$_1$-C$_4$alkyl or C$_1$-C$_4$alkoxy, R$_5$ is hydrogen or C$_1$-C$_4$alkyl and X is an oxygen or sulfur atom.

(b) Compounds wherein R$_1$ is C$_1$-C$_4$alkyl, allyl, cyclopropyl or C$_1$-C$_3$alkoxy, R$_2$ is C$_1$-C$_4$alkyl, R$_3$ is a pyrazinyl, pyrimidinyl, pyridazinyl, triazinyl, quinoxalinyl or quinolinyl radical, each of which is bound through a carbon atom and is unsubstituted or substituted by one to three substituents selected from the group consisting of C$_1$-C$_4$alkyl, C$_1$-C$_4$haloalkyl, C$_1$-C$_4$alkoxy, C$_1$-C$_4$alkylthio, di(C$_1$-C$_3$alkyl)amino, halogen and phenyl, R$_4$ is hydrogen, C$_1$-C$_4$alkyl or C$_1$-C$_4$alkoxy, R$_5$ is hydrogen or C$_1$-C$_4$alkyl and X is an oxygen or sulfur atom.

(c) Compounds wherein R$_1$ is C$_1$-C$_4$alkyl, allyl, cyclopropyl or methoxy, R$_2$ is methyl, R$_3$ is a pyrimidinyl, pyrazinyl or pyridazinyl radical, each of which is bound through a carbon atom and is unsubstituted or substituted by one to three substituents selected from the group consisting of C$_1$-C$_4$alkyl, trifluoromethyl, methoxy, methylthio, chlorine and phenyl, R$_4$ is hydrogen, C$_1$-C$_4$alkyl or C$_1$-C$_4$alkoxy, R$_5$ is hydrogen or C$_1$-C$_4$alkyl and X is an oxygen or sulfur atom and the molecule fragment —OR$_3$ is in the meta- or para-position to the nitrogen atom of the carbamoyl group.

(d) Compounds wherein R$_1$ is methyl or methoxy, R$_2$ is methyl, R$_3$ is a pyrimidinyl ring which is bound through a carbon atom and is unsubstituted or substituted by one or two substituents selected from the group consisting of C$_1$-C$_4$alkyl, C$_1$-C$_4$haloalkyl, halogen and phenyl, R$_4$ is hydrogen, C$_1$-C$_4$alkyl or C$_1$-C$_4$alkoxy, R$_5$ is hydrogen or methyl and X is an oxygen or sulfur atom and the molecule fragment —OR$_3$ is in the meta- or para-position to the nitrogen atom of the carbamoyl group.

(e) Compounds wherein R$_1$ is methyl, R$_2$ is methyl, R$_3$ is a pyrimidinyl ring which is bound through a carbon atom and is substituted by one or two substituents selected from the group consisting of methyl, trifluoromethyl, chlorine and phenyl, R$_4$ is hydrogen, methyl, isopropyl, methoxy or ethoxy, R$_5$ is hydrogen or methyl and X is an oxygen or sulfur atom and the molecule fragment —OR$_3$ is in the meta- or para-position to the nitrogen atom of the carbamoyl group.

(f) Compounds wherein R$_1$ is methyl, R$_2$ is methyl, R$_3$ is a pyrimidinyl ring which is bound through a carbon atom and is substituted by one trifluoromethyl group or is substituted by not more than two substituents, namely by one trifluoromethyl group and by one further substituent selected from the group consisting of methyl, trifluoromethyl, chlorine and phenyl, R$_4$ is hydrogen, methyl, isopropyl or methoxy, R$_5$ is hydrogen or methyl and X is an oxygen or sulfur atom and the molecule fragment —OR₃ is in the para-position to the nitrogen atom of the carbamoyl group.

Preferred individual compounds are:
1,3-dimethyl-5-[4-(6-chloro-1-oxypyridazin-3-yloxy)-phenylcarbamoyl]barbituric acid,
1,3-dimethyl-5-[4-(3-methylpyrazin-2-yloxy)phenylcarbamoyl]barbituric acid,
1,3-dimethyl-5-[4-(3-chloropyrazin-2-yloxy)phenylcarbamoyl]barbituric acid,
1,3-dimethyl-5-[4-(3-methylpyrazin-2-yloxy)phenylcarbamoyl]-2-thiobarbituric acid,
1,3-dimethyl-5-[4-(6-trifluoromethylpyrimidin-4-yloxy)phenylcarbamoyl]barbituric acid,
1,3-dimethyl-5-[4-(4-trifluoromethylpyrimidin-2-yloxy)phenylcarbamoyl]barbituric acid,
1,3-dimethyl-5-[4-(2-trifluoromethylpyrimidin-4-yloxy)phenylcarbamoyl]-2-thiobarbituric acid,
1,3-dimethyl-5-[4-methoxy-3-(6-trifluoromethylpyrimidin-4-yloxy)phenylcarbamoyl]-2-thiobarbituric acid,
1,3-dimethyl-5-[3-methoxy-4-(4-trifluoromethylpyrimidin-2-yloxy)phenylcarbamoyl]-2-thiobarbituric acid,
1,3-dimethyl-5-[2-isopropyl-4-(6-trifluoromethylpyrimidin-4-yloxy)phenylcrbamoyl]barbituric acid,
1,3-dimethyl-5-[2,6-dimethyl-4-(2-trifluoromethylpyrimidin-4-yloxy)phenylcarbamoyl]barbituric acid,
1,3-dimethyl-5-[3-methoxy-4-(2-trifluoromethylpyrimidin-4-yloxy)phenylcarbamoyl]barbituric acid,
1,3-dimethyl-5-[4-(2-methyl-6-trifluoromethylpyrimidin-4-yloxy)phenylcarbamoyl]barbituric acid,
1,3-dimethyl-5-[2-isopropyl-4-(6-trifluoromethylpyrimidin-4-yloxy)phenylcarbamoyl]-2-thiobarbituric acid,
1,3-dimethyl-5-[2,6-dimethyl-4-(2-trifluoromethylpyrimidin-4-yloxy)phenylcarbamoyl]-2-thiobarbituric acid,
1,3-dimethyl-5-[4-(5-chloropyrimidin-2-yloxy)phenylcarbamoyl]barbituric acid,
1,3-dimethyl-5-[3-methoxy-4-(5-methyl-4-trifluoromethylpyrimidin-2-yloxy)phenylcarbamoyl]barbituric acid,
1,3-dimethyl-5-[4-(5-phenyl-4-trifluoromethylpyrimidin-2-yloxy)phenylcarbamoyl]barbituric acid,
1,3-dimethyl-5-[4-(4-methyl-6-trifluoromethylpyrimidin-2-yloxy)phenylcarbamoyl]barbituric acid,
1,3-dimethyl-5-[4-(4-methyl-6-trifluoromethylpyrimidin-2-yloxy)phenylcarbamoyl]-2-thiobarbituric acid,
1,3-dimethyl-5-[4-(6-methyl-2-trifluoromethylpyrimidin-4-yloxy)phenylcarbamoyl]barbituric acid and
1,3-dimethyl-5-[4-(2-trifluoromethylpyrimidin-4-yloxy)phenylcarbamoyl]barbituric acid.

Surprisingly, it has now been found that the novel compounds of formula I of this invention possess a very favourable activity spectrum against helminths which are parasites of animals, especially against helminths which parasites in warm-blooded animals, in particular in mammals. The compounds of Formula I can be employed very successfully against nematodes as well as against cestodes and trematodes. A particular feature of the novel compounds is that they are fully effective also against benzimidazole-resistant helminths, in particular against thiabendazole-resistant helminths ("thiabendazole" denotes the compound 2-(thiazol-4-yl)benzimidazole).

The compounds of formula I are prepared by:
(a) Reacting a compound of formula II

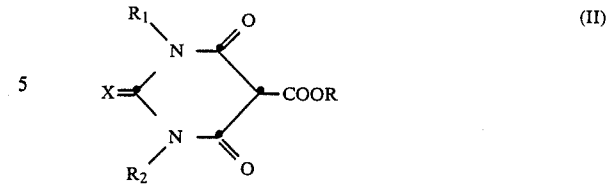

wherein $R_1$, $R_2$ and X are as defined for formula I and R is $C_1-C_5$alkyl, or phenyl which is unsubstituted or substituted by nitro, with a compound of formula III

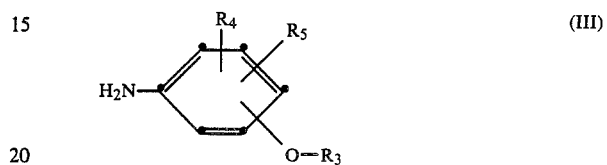

wherein $R_3$, $R_4$ and $R_5$ are as defined for formula I, or
(b) reacting a compound of formula IV

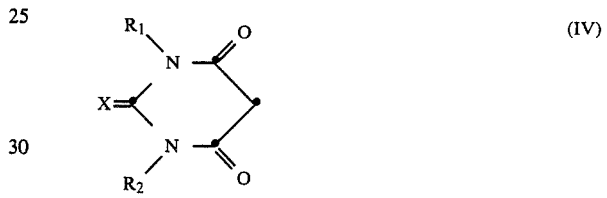

wherein $R_1$, $R_2$ and X are as defined for formula I, with a compound of formula V

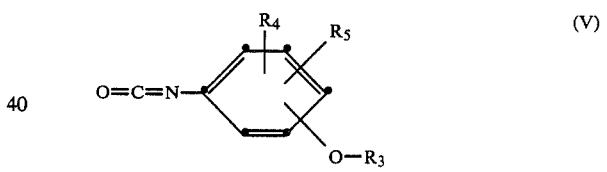

wherein $R_3$, $R_4$ and $R_5$ are as defined for formula I, or
(c) reacting a compound of formula IV, wherein $R_1$, $R_2$ and X are as defined for formula I, with a compound of formula VI

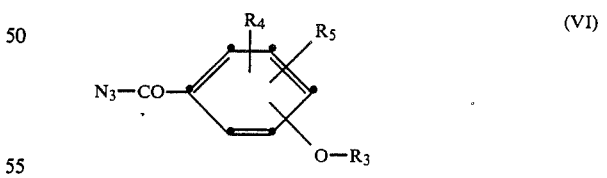

wherein $R_3$, $R_4$ and $R_5$ are as defined for formula I, or
(d) reacting a compound of formula VII

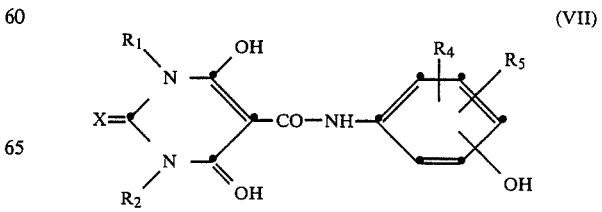

wherein $R_1$, $R_2$, $R_4$, $R_5$ and X are as defined for formula I, with a compound of formula VIII $$Q-R_3 \qquad (VIII)$$

wherein Q is a customary leaving group and $R_3$ is as defined for formula I, in the presence of a base, or (e) to prepare compounds of formula I, wherein at least one of the substituents $Z_1$, $Z_2$, $Z_3$, $Z_4$ and $Z_5$ is hydrogen, $C_1$–$C_4$alkoxy, $C_1$–$C_4$alkylthio, $C_1$–$C_3$alkylamino or di($C_1$–$C_3$alkyl)amino, reacting a compound of formula IX

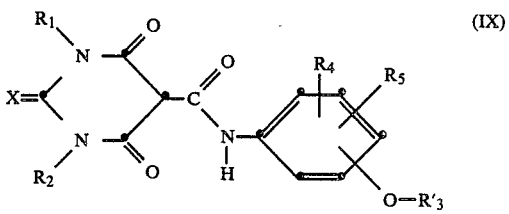

wherein $R_1$, $R_2$, $R_4$, $R_5$ and X are as defined for formula I and $R'_3$ is a heteroaromatic 6-membered ring which contains 2 to 3 nitrogen atoms, or is a heteroaromatic ring which is fused to a benzene ring and which contains 1 to 3 nitrogen atoms, with the ring or the heterocyclic moiety of the ring system being substituted by halogen, preferably chlorine, or methylsulfonyl, with a compound of formula X $$Z-H \qquad (X)$$

wherein Z is $C_1$–$C_4$alkoxy, $C_1$–$C_4$alkylthio, $C_1$–$C_3$alkylamino or di($C_1$–$C_3$alkyl)amino.

Process variants (a) and (c) are carried out at reaction temperatures in the range from 50° to 250° C., preferably from 70° to 220° C. Variant (b) requires reaction temperatures in the range from 0° to 220° C., preferably from 0° to 200° C. Variant (d) is carried out at reaction temperatures in the range from 50° to 250° C., preferably from 80° to 150° C., in an inert solvent or diluent. Reactions (a), (b) and (c) may be carried out under normal or increased pressure and in the absence or, preferably, presence of an inert solvent or diluent. In some cases, the reactions are conveniently carried out in the presence of a base.

It is most advantageous to carry out variant (e) in the following manner: (e₁) if Z is hydrogen, by reacting a compound of formula IX with a compound of formula X in the presence of a catalyst such as Raney nickel or palladium on active carbon; (e₂) if Z is $C_1$–$C_4$alkoxy or $C_1$–$C_4$alkylthio, by reacting a compound of formula IX with a compound of formula X in the presence of a base or, after conversion of Z—H in conventional manner into a salt Z—M⊕, wheren M⊕ is a suitable cation such as Na⊕ or K⊕, in an inert solvent and at a temperature in the range from 20° to 200° C., preferably from 50° to 150° C.; or (e₃) if Z is $C_1$–$C_3$alkylamino or di($C_1$–$C_3$alkyl)amino, in the presence of a base or employing Z—H in excess and at a temperature in the range indicated above (e₂).

The salts of compounds of formula I are prepared by conventional neutralisation of the free acid with a base, in particular a physiologically acceptable base. Preferred salts are alkali metal salts such as sodium, potassium or lithium salts, as well as ammonium salts and trialkylamine salts. e.g. the preferred triethylamine salt.

Neutralisation is effected in an inert polar solvent, e.g. an alkanol, an ester or an ethereal compound.

N oxides of compounds of formula I can be prepared in a manner known per se, e.g. by oxidising resultant compounds of formula I with peroxides.

The intermediates of formulae III and VII which have been specially developed for the preparation of compounds of formula I in accordance with process variants (a) and (d) are novel and constitute an object of the present invention. The processes described below for the preparation of said intermediates of formulae III and VII likewise constitute an object of the present invention.

The compounds of formula VII are prepared by a method analogous to known methods by reacting a compound of formula II, wherein $R_1$, $R_2$ and X are defined for formula I, with the meanings listed in Table 1 being preferred, and R is $C_1$–$C_5$alkyl, or phenyl which is unsubstituted or substituted by nitro, with a compound of formula XI

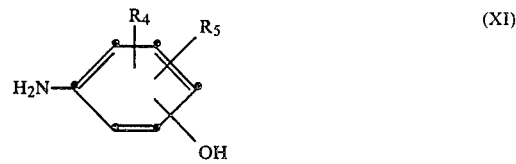

wherein $R_4$ and $R_5$ are as defined for formula I, with the meanings listed in Table 1 being preferred. The reaction is carried out under the same conditions as those indicated above under process variant (a) for the reaction of compounds of formula II with compounds of formula III.

The compounds of formula III are prepared by a method analogous to that of process variant (d) by reacting a compound of formula XI, wherein $R_4$ and $R_5$ are as defined for formula I, with the meanings listed in Table 1 being preferred, with a compound of formula VIII, wherein $R_3$ is as defined for formula I, with the meanings listed in Table 1 being preferred, and Q is a customary leaving group. The reaction is carried out under the same conditions as those indicated above under process variant (d) for the reaction of compounds of formula VII with compounds of formula VIII.

Q in formula VIII is one of the customary leaving groups, e.g. halogen, preferably chlorine, bromine or iodine; a sulfonyloxy group, preferably benzenesulfonyloxy, paratosyloxy or lower alkylsulfonyloxy, preferably mesyloxy; or an acyloxy group such as trifluoroacetyloxy. Q is also a hydroxy group or, in accordance with "Synthesis" 1979, pp. 561–569, the radical

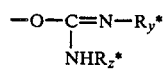

wherein $R_y^*$ and $R_z^*$ as organic radicals are for example isopropyl or p-tolyl. These radicals may, however, also be other lower alkyl radicals or unsubstituted or substituted phenyl, with suitable substituents being for example those radicals listed above under $Z_4$ and $Z_5$.

Examples of representatives of compounds of formula III are the following:

4-(3-methylpyrazin-2-yloxy)aniline, m.p. 108°–109° C.;
4-(3-chloropyrazin-2-yloxy)aniline, m.p. 130°–131° C.;

4-(6-chloroquinoxalin-2-yloxy)aniline, m.p. 107°–112° C.;
4-(pyrimidin-2-yloxy)aniline, m.p. 125°–129° C.;
4-(4-chloropyrimidin-2-yloxy)aniline, oil;
4-(4,6-dimethylpyrimidin-2-yloxy)aniline, m.p. 92°–96° C.;
4-(6-chloropyrimidin-4-yloxy)aniline, oil;
4-(2-methylthio-6-methylpyrimidin-4-yloxy)aniline, oil;
4-(2-tert-butyl-6-chloropyrimidin-4-yloxy)aniline, oil;
4-(quinolin-2-yloxy)aniline;
3-(6-chloroquinoxalin-2-yloxy)aniline;
4-(3-methoxyquinoxalin-2-yloxy)aniline;
3-(quinolin-2-yloxy)aniline;
2,6-dimethyl-4-(pyrazin-2-yloxy)aniline;
3-(6-chloropyridazin-3-yloxy)aniline;
4-(4,6-dimethoxy-1,3,5-triazin-2-yloxy)aniline;
4-(4,6-dimethylthio-1,3,5-triazin-2-yloxy)aniline.

Examples of suitable solvents or diluents for the preparation of the compounds of the invention are ethers and ethereal compounds such as dialkyl ethers (diethyl ether, diisopropyl ether, tert-butylmethyl ether etc.), anisole, dioxane, tetrahydrofuran; aliphatic and aromatic hydrocarbons such as benzene, toluene, petroleum ether; halogenated hydrocarbons such as chlorobenzene, methylene chloride, chloroform, ethylene chloride, carbon tetrachloride, tetrachloroethylene; nitriles such as acetonitrile and propionitrile; N,N-dialkylated amides such as dimethylformamide; dimethyl sulfoxide; ketones such as acetone, diethyl ketone and methyl ethyl ketone; as well as, in particular for process variant (d), water and alcohols such as methanol, ethanol, isopropanol or butanol; and in general mixtures of such solvents with each other.

Suitable bases are organic and inorganic bases, e.g. preferably tertiary amines such as trialkylamines (trimethylamine, triethylamine, tripropylamine, etc.), pyridine and pyridine bases (e.g. 4-dimethylaminopyridine, 4-pyrrolidylaminopyridine etc.), picolines and lutidines, as well as oxides, hydroxides, carbonates and bicarbonates of alkali metals and alkaline earth metals (e.g. CaO, BaO, NaOH, KOH, Ca(OH)$_2$, KHCO$_3$, NaHCO$_3$, Ca(HCO$_3$)$_2$, K$_2$CO$_3$, Na$_2$CO$_3$ etc.), and also acetates such as CH$_3$COONa or CH$_3$COOK. Further suitable bases are alkali metal alcoholates, e.g. sodium ethylate, sodium propylate, potassium tert-butylate or sodium methylate. For process variants (a), (b) and (c) it is advantageous to add the base in 10 to 100% of the equimolar amount, for process variant (d) in 200% of the equimolar amount, based on the reactants.

In some cases it may be of advantage to carry out the reaction in an inert gas atmosphere. Suitable inert gases are e.g. nitrogen, helium, argon or carbon dioxide.

Compounds of formula I which are present as salt can be converted into the free form by methods known per se.

With the exception of the compounds of formula III employed in process variant (a) and of the compounds of formula VII employed in process variant (d), the starting materials in process variants (a), (b), (c), (d) and (e) are known (q.v. e.g. Chem. Ber. 54, 1038 [1921]) or they can be prepared in corresponding manner to known ones.

The described preparatory process, including all variants (a), (b), (c), (d) and (e), constitutes an object of this invention.

The compounds of formula I may exist in different tautomeric forms, viz. in the keto or enol form or in a mixture of these forms. The present invention relates both to the individual tautomers and to their mixtures, as well as to the salts of each of these forms and to the preparation thereof. The same also applies to the N oxides of compounds of formula I.

The invention also relates to a method of protecting animals from attack by parasitic helminths, which comprises applying the compounds of formula I, or the formulations containing them, as additives to the solid or liquid feeds or also orally in solid or liquid form, by injection or by the pour-on method.

The compounds of formula I may be used in all tautomeric forms and mixtures thereof, or in the form of their salts, in each of the helminth control methods or anthelmintic compositions of this invention.

Among the endoparasites which occur in warm-blooded animals, the helminths cause severe damage. For example, animals attacked by these parasites are not only retarded in their growth, but in some cases suffer such harmful physiological effects that they die. It is therefore of great importance to develop therapeutic agents which are suitable for controlling helminths and their development stages and to prevent attack by these parasites. Particularly dangerous helminth infestations are those caused in the gastrointestinal tract and other organs by parasitic nematodes, cestodes and trematodes, and especially in ruminants such as sheep, cattle and goats, as well as horses, pigs, deer, dogs, cats and poultry.

The damage caused by helminthiases can be substantial whenever herds of cattle fall victim to chronic and, in particular, epidemic attack. Such damage takes the form inter alia of diminution of useful performance, weakened resistance and increased mortality. The control and prevention of helminth infestation are therefore of the utmost importance to avoid or reduce such damage, especially damage having serious economic consequences.

Throughout this specification, the term "helminths" will be understood as meaning in particular parasitic worms which belong to the phyla Platyhelminthes (cestodes, trematodes) and Nemathelminthes (nematodes and related species), i.e. cestodes, trematodes and nematodes of the gastrointestinal tract and other organs (e.g. liver, lungs, kidneys, lymphatic vessels, blood etc.). Although a range of compounds having anthelminthic activity are known and have been proposed for controlling the different helminth species, they are not entirely satisfactory, either because it is not possible to exploit their activity spectrum fully when administered in well tolerated doses or because they exhibit undesirable side-effects or characteristics when administered in therapeutic doses. In this regard, the increasing resistance being encountered at the present time to specific classes of compounds is an ever more significant factor. Although, for example, the prior art compound "albendazole" (British Pat. specification No. 1 464 326; Am. J. Vet. Res. 38, 1425–1426 (1977); Am. J. Vet. Res. 37, 1515–1516 (1976); Am. J. Vet. Res. 38, 807–808 (1977); Am. J. Vet. Res. 38, 1247–1248 (1977)) has a limited activity spectrum as anthelmintic when administered to ruminants, its activity against benzimidazole-resistant nematodes and adult liver flukes is inadequate. In particular, the pathologically important immature migratory forms of the last mentioned parasites are not attacked when the compound is administered in doses which are tolerated by the host animal.

Surprisingly, it has now been found that the compounds of formula I not only have, as mentioned above, a potent anthelmintic activity with a broad activity spectrum against nematodes, cestodes and trematodes but have, in addition, a low toxicity to warm-blooded animals.

The novel compounds of formula I of the invention are suitable e.g. for controlling parasitic nematodes of the orders (according to the classification of K. I. Skrajaban)

Rhabditida
Ascaridida
Spirurida
Trichocephalida or for controlling cestodes of the orders (according to the classification of Wardle & McLeod)

Cyclophyllidae
Pseudophyllidae or for controlling trematodes of the order

Digenea in domestic animals and productive livestock such as cattle, sheep, goats, horses, pigs, cats, dogs and poultry. The compounds of formula I may be administered to the animals in both individual and repeated doses. Depending on the species of animal, the individual doses are preferably administered in amounts ranging from 1 to 500 mg per kg of body weight. A better activity is sometimes attained by protracted administration, or lower total doses may suffice.

The compositions of this invention are prepared by bringing the compounds of formula I into contact with liquid and/or solid formulation adjuvants by stepwise mixing or grinding such that the formulation is able to exert its anthelmintic activity in optimum manner in accordance with the mode of application.

The formulation steps may be complemented by kneading, granulating and, if desired, pelleting.

Suitable formulation adjuvants are for example solid carriers, solvents and, optionally, surface-active compounds (surfactants).

The following formulation adjuvants are employed for preparing the compositions of the invention: solid carriers, e.g. kaolin, talc, bentonite, common salt, calcium phosphate, carbohydrates, cellulose powder, cottonseed meal, polyethylene glycol ether, optionally binders such as gelatin, soluble cellulose derivatives, if desired with the addition of surface-active compounds such as ionic or non-ionic dispersants; natural mineral fillers such as calcite, montmorillonite or attapulgite. To improve the physical properties it is also possible to add highly dispersed silicic acid or highly dispersed adsorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant material.

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils, epoxidised vegetable oils such as epoxidised coconut oil or soybean oil; or water.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acids and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylaryl-sulfonates are the sodium, calcium or triethanolamine salts of dodecylbenzenesulfonic acid, dibutylnaphthalenesulfonic acid or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in:

"McCutcheon's Detergents and Emulsifiers Annual", MC Publishing Corp., Ridgewood, N.J., 1981;

Stache, H., "Tensid-Taschenbuch" (Handbook of Surfactants), Carl Hanser Verlag, Munich/Vienna, 1981.

Suitable binders for tablets and boluses are chemically modified natural polymers which are soluble in water or alcohol, e.g. starch, cellulose or protein derivatives (e.g. methyl cellulose, carboxymethyl cellulose, ethyl hydroxyethyl cellulose, proteins such as zein, gelatin and the like), as well as synthetic polymers such as polyvinyl alcohol, polyvinyl pyrrolidone etc. Tablets also contain fillers (e.g. starch, microcrystalline cellulose, sugar, lactose etc.), glidants and disintegrators.

If the anthelmintic compositions are in the form of feed concentrates, then suitable carriers are for example production feeds, cereal feeds or protein concentrates. In addition to the active ingredients, such feeds can contain additives, vitamins, antibiotics, chemotherapeutical agents or other pesticides, in particular bacteriostats, fungistats, coccidiostats or also hormone preparations, substances having anabolic action or other substances which promote growth, enhance the quality of the flesh of slaughter animals, or which are otherwise beneficial to the organism. If the compositions or the compounds of formula I contained therein are added direct to the solid or liquid feed, then the ready prepared feed contains the active ingredient preferably in a concentration of about 0.0005 to 0.02 percent by weight (5-200 ppm).

The compositions of the invention are administered to the animals to be treated perorally, parenterally, subcutaneously or topically, and are in the form of solutions, emulsions, suspensions (drenches), powders, tablets, boluses and capsules.

The anthelmintic compositions of this invention usually contain 0.1 to 99% by weight, preferably 0.1 to 95% by weight, of a compound of formula I, and 99.9 to 1% by weight, preferably 99.9 to 5% by weight, of a solid or liquid adjuvant, including 0 to 25% by weight, preferably 0.1 to 25% by weight, of a surfactant.

Whereas commercial products will be preferably formulated as concentrates, the end user will normally employ dilute formulations.

The compositions may also contain further ingredients such as stabilisers, antifoams, viscosity regulators, binders, tackifiers or other active ingredients in order to obtain special effects.

Such anthelmintic compositions employed by the end user likewise constitute an object of the present invention.

The invention is illustrated in more detail by the following non-limitative Examples.

1. PREPARATORY EXAMPLES

1.1.

1,3-Dimethyl-5-[4-(2-isopropyl-6-methylpyrimidin-4-yloxy)phenylcarbamoyl]barbituric acid 3.0 g (0.013 mole) of 1,3-dimethyl-5-ethoxycarbonylbarbituric acid and 3.2 g (0.013 mole) of 4-(2-isopropyl-6-methylpyrimidin-4-yloxy)aniline are suspended in 30 ml of toluene and heated for 18 hours at reflux temperature in an inert gas atmosphere (nitrogen). After cooling, the precipitate is isolated by filtration, washed with alcohol and dried.

Yield: 4.4 g (80% of theory); m.p.: 147°-149° C.

1.2.

1,3-Dimethyl-5-[4-(3,5-dichloropyrimidin-4-yloxy)phenylcarbamoyl]barbituric acid 7.8 g (0.050 mole) of 1,3-dimethylbarbituric acid and 13.5 g (0.050 mole) of 4-(2-isopropyl-6-methylpyrimidin-4-yloxy)phenylisocyanate are suspended in 50 ml of xylene, and 1 g (0.010 mole) of triethylamine is then added dropwise. The temperature rises to 45° to 50° C. After the addition of a further 50 ml of xylene, the mixture is stirred for 18 hours at this temperature. A third of the xylene is then distilled off. After cooling, the precipitate is isolated by filtration, washed with xylene, suspended several times in water and finally thoroughly washed with water and dried.

1.3.

1,3-Dimethyl-5-[4-(2-isopropyl-6-methylpyrimidin-4-yloxy)phenylcarbamoyl]barbituric acid 1.56 g (0.01 mole) of 1,3-dimethylbarbituric acid are added to a solution of 3.85 g (0.01 mole) of 4-(2-isopropyl-6-methylpyrimidin-4-yloxy)benzoylazide in 50 ml of toluene. Subsequently, a solution of 0.02 g (0.002 mole) of triethylamine in 5 ml of toluene is added dropwise at room temperature. The mixture is then stirred for 1 hour at 50° C. and the temperature is subsequently increased stepwise, each time by 20° C., until the reflux temperature is reached. The mixture is held at reflux temperature until the evolution of nitrogen ceases. After cooling, the precipitate is isolated by filtration, washed with ethanol, suspended several times in 1N HCl and subsequently thoroughly washed with water and dried.

Yield: 3 g (60% of theory); m.p.: 147°-149° C.

The starting material 4-(2-isopropyl-6-methylpyrimidin-4-yloxy)benzoylazide is prepared as follows:

3.4 g (0.031 mole) of ethyl chloroformate are added at 0° C. to 6.4 g (0.024 mole) of 4-(2-isopropyl-6-methylpyrimidin-4-yloxy)benzoic acid in 40 ml of acetone, in the presence of 2.9 g (0.028 mole) of triethylamine, followed by the addition of 2.4 g (0.036 mole) of sodium azide in 8 ml of water. After stirring for 3 hours at 0° C., the mixture is poured into 100 ml of water and extracted with 60 ml of toluene. The toluene phase is separated, dried over sodium sulfate at 0° C. and, after filtration, is used for the reaction described above.

1.4.

1,3-Dimethyl-5-[4-(2-isopropyl-6-methylpyrimidin-4-yloxy)phenylcarbamoyl]barbituric acid 1 g (0.010 mole) of triethylamine is added dropwise to a suspension of 7.8 g (0.050 mole) of 1,3-dimethylbarbituric acid and 19.2 g (0.050 mole) of 4-(2-isopropyl-6-methylpyrimidin-4-yloxy)benzoylazide in 50 ml of xylene. The temperature rises to 45° to 50° C. After the addition of a further 50 ml of xylene, the mixture is stirred at this temperature for 18 hours. A third of the xylene is then distilled off. After cooling, the precipitate is isolated by filtration, washed with xylene, suspended several times in water and finally thoroughly washed with water and dried.

Yield: 15 g (60% of theory); m.p.: 147°-149° C.

1.5. 1,3-Dimethyl-5-[4-(3-methylpyrazin-2-yloxy)phenylcarbamoyl]-2-thiobarbituric acid 2.5 g (10 mmol) of 1,3-dimethyl-5-ethoxycarbonyl-2-thiobarbituric acid, 2.0 g (10 mmol) of 4-(3-methylpyrazin-2-yloxy)aniline and 30 ml of ethanol are mixed and, with stirring, are kept at 60° C. for 20 hours. The mixture is then allowed to cool and the crystalline precipitate formed is isolated by filtration, washed with ethanol and dried in vacuo at 80° C.

Yield: 1.4 g; m.p.: 167°–169° C.

1.6. 1,3-Dimethyl-5-[4-(6-methoxypyridazin-3-yloxy)phenylcarbamoyl]barbituric acid 4.0 g (0.06 mole) of 85% KOH are added to 8.7 g (0.03 mole) of 1,3-dimethyl-5-(4-hydroxyphenylcarbamoyl)barbituric acid in 70 ml of toluene and 50 ml of dimethyl sulfoxide. The mixture is dewatered with a water separator at reflux temperature. After the toluene has been distilled off, 4.3 g (0.03 mole) of 3-chloro-6-methoxypyridazine are added. The bath temperature is increased gradually until a temperature in the range from 120° to 140° C. is reached, and the mixture is kept at this temperature for 2 hours. The mixture is then cooled to 80° C., neutralised with dilute hydrochloric acid, cooled to room temperature and diluted with water. The precipitate is isolated by filtration, washed with water and dried.

Yield: 7 g (60% of theory); m.p.: 237° C.

1.7. 1,3-Dimethyl-5-[4-(6-methoxypyridazin-3-yloxy)phenylcarbamoyl]barbituric acid The equimolar amount of sodium methylate is added at room temperature to 1.0 g (0.0025 mole) of 1,3-dimethyl-5-[4-(6-chloropyridazin-3-yloxy)phenylcarbamoyl]barbituric acid in 20 ml of methanol. The mixture is heated under reflux for 5 hours, then cooled, diluted with water and filtered. The filtrate is washed with water and dried.

Yield: 0.7 g (70% of theory); m.p.: 237° C.

Preparation of the starting 1,3-dimethyl-5-[4-(6-chloropyridazin-3-yloxy)phenylcarbamoyl]barbituric acid:

7.3 g (0.032 mole) of 1,3-dimethyl-5-ethoxycarbonylbarbituric acid and 7.1 g (0.032 mole) of 4-(6-chloropyridazin-3-yloxy)aniline are suspended in 100 ml of toluene and heated for 3 hours at reflux temperature in an inert gas atmosphere (nitrogen), whereupon ethanol escapes. After cooling to 80° C., the mixture is diluted with 80 ml of ethanol, cooled and filtered. The filtrate is recrystallised in a mixture of chloroform and ethanol.

Yield: 4.0 g (30% of theory); m.p. 265°–267° C.

1.8. 1,3-Dimethyl-5-[4-(quinolin-2-yloxy)phenylcarbamoyl]barbituric acid 6.1 g of 4-(quinolin-2-yloxy)aniline and 5.8 g of 1,3-dimethyl-5-ethoxycarbonylbarbituric acid are heated under reflux in 50 ml of toluene. When the temperature is at 80° C., a thick crystalline slurry is formed which at 120° C. is again of a stirrable consistency. After stirring for 3 hours, the mixture is cooled and the crystals are isolated by suction filtration.

Yield: 9.9 g in the form of beige-coloured crystals; m.p.: 220°–222° C.

The following compounds of formula I listed in Table 1 together with the compounds of Examples 1.1 to 1.8 above can also be prepared by methods analogous to those described above:

TABLE 1

Compounds of the formula

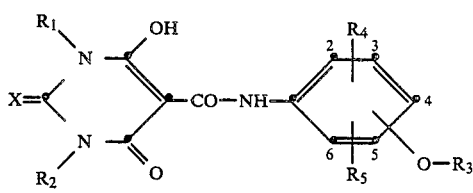

| Comp. | $R_1$ | $R_2$ | $R_4$ | $R_5$ | Position X | —O—$R_3$ | $R_3$ | Physical data [°C.] |
|---|---|---|---|---|---|---|---|---|
| 1 | $CH_3$ | $CH_3$ | H | H | O | 4 | 3-methylpyrazin-2-yl | m.p. 185–187 |
| 2 | $CH_3$ | $CH_3$ | H | H | O | 4 | 3-chloropyrazin-2-yl | m.p. 206–208 |
| 3 | $CH_3$ | $CH_3$ | H | H | O | 4 | 6-chloroquinoxalin-2-yl | m.p. 228–231 |
| 4 | $CH_3$ | $CH_3$ | H | H | O | 4 | pyrimidin-2-yl | m.p. 197 |
| 5 | $CH_3$ | $CH_3$ | H | H | O | 4 | 4,6-dimethylpyrimidin-2-yl | m.p. 199–203 |
| 6 | $CH_3$ | $CH_3$ | H | H | O | 4 | 4-chloropyrimidin-2-yl | m.p. 226–228 |
| 7 | $CH_3$ | $CH_3$ | H | H | O | 4 | 6-chloropyrimidin-4-yl | m.p. 194–196 |
| 8 | $CH_3$ | $CH_3$ | H | H | O | 4 | quinolin-2-yl | m.p. 220–222 |
| 9 | $CH_3$ | $CH_3$ | H | H | S | 4 | 3-methylpyrazin-2-yl | m.p. 167–169 |
| 10 | $CH_3$ | $CH_3$ | H | H | O | 4 | 6-chloropyridazin-3-yl | m.p. 265–267 |
| 11 | $CH_3$ | $CH_3$ | H | H | O | 4 | 6-methoxypyridazin-3-yl | m.p. 237 |
| 12 | $CH_3$ | $CH_3$ | H | H | O | 4 | 2-isopropyl-6-methylpyrimidin-4-yl | m.p. 147–149 |
| 13 | $CH_3$ | $CH_3$ | H | H | O | 4 | 2-methylthio-6-methylpyrimidin-4-yl | m.p. 204–205 |
| 14 | $CH_3$ | $CH_3$ | H | H | O | 4 | 2-tert-butyl-6-chloropyrimidin-4-yl | m.p. 158–160 |
| 15 | $CH_3$ | $CH_3$ | H | H | O | 4 | 3,5-dichloropyridazin-4-yl | |
| 16 | $CH_3$ | $CH_3$ | H | H | O | 4 | 3-chloro-4-methylthiopyridazin-5-yl | |
| 17 | $CH_3$ | $CH_3$ | H | H | O | 4 | 3,6-dichloropyridazin-4-yl | |
| 18 | $CH_3$ | $CH_3$ | H | H | O | 4 | 3-chloro-4-methylthiopyridazin-6-yl | |
| 19 | $CH_3$ | $CH_3$ | H | H | O | 4 | 3,5,6-trichloropyridazin-4-yl | |
| 20 | $CH_3$ | $CH_3$ | H | H | O | 4 | 3-chloro-4-methylpyridazin-6-yl | |
| 21 | $OCH_3$ | $CH_3$ | H | H | O | 4 | 3-methylpyrazin-2-yl | |
| 22 | $CH_3$ | $CH_3$ | H | H | S | 4 | 5-chloropyridazin-3-yl | |

TABLE 1-continued

Compounds of the formula

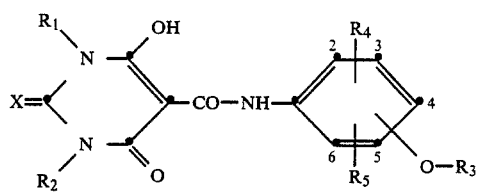

| Comp. | R₁ | R₂ | R₄ | R₅ | X | Position —O—R₃ | R₃ | Physical data [°C.] |
|---|---|---|---|---|---|---|---|---|
| 23 | OCH₃ | CH₃ | H | H | O | 4 | 6-methoxypyridazin-3-yl | |
| 24 | CH₃ | CH₃ | 3-OCH₃ | H | O | 4 | 6-methoxypyridazin-3-yl | |
| 25 | CH₃ | CH₃ | H | H | O | 4 | 6-methylthiopyridazin-3-yl | |
| 26 | CH₃ | CH₃ | H | H | O | 4 | 6-methylaminopyridazin-3-yl | |
| 27 | CH₃ | CH₃ | H | H | O | 4 | 2-methyl-6-chloropyrimidin-4-yl | m.p. 222–223 |
| 28 | CH₃ | CH₃ | H | H | O | 4 | 2-methylthio-6-chloropyrimidin-4-yl | |
| 29 | CH₃ | CH₃ | H | H | O | 4 | 2-methylthio-5-phenyl-6-chloropyrimidin-4-yl | m.p. 207–208 |
| 30 | CH₃ | CH₃ | H | H | O | 4 | 2-methylthiopyrimidin-4-yl | m.p. 191–193 |
| 31 | OCH₃ | CH₃ | H | H | O | 4 | 2-methylthio-6-methylpyrimidin-4-yl | |
| 32 | CH₃ | CH₃ | H | H | S | 4 | 2-tert-butyl-6-chloropyrimidin-4-yl | |
| 33 | CH₃ | CH₃ | H | H | O | 4 | 4-chloro-6-methylpyrimidin-2-yl | |
| 34 | CH₃ | CH₃ | H | H | O | 4 | 4-methoxy-6-methylpyrimidin-2-yl | |
| 35 | CH₃ | CH₃ | H | H | O | 4 | 4,6-dichloropyrimidin-2-yl | |
| 36 | CH₃ | CH₃ | H | H | O | 4 | 2,6-dimethylpyrimidin-4-yl | m.p. 226–227 |
| 37 | CH₃ | CH₃ | H | H | O | 4 | 4-chloro-5,6-dimethylpyrimidin-2-yl | |
| 38 | CH₃ | CH₃ | H | H | O | 4 | 4-methylpyrimidin-2-yl | m.p. 196–198 |
| 39 | CH₃ | CH₃ | H | H | O | 4 | 4-chloro-6-dimethylamino-1,3,5-triazin-2-yl | m.p. 230 |
| 40 | CH₃ | CH₃ | H | H | O | 4 | 4-chloro-5-trifluoromethylpyrimidin-2-yl | |
| 41 | CH₃ | CH₃ | H | H | O | 4 | 2-chloro-5-trifluoromethylpyrimidin-4-yl | |
| 42 | CH₃ | CH₃ | H | H | O | 4 | 6-trifluoromethylpyrimidin-4-yl | m.p. 178–179 |
| 43 | CH₃ | CH₃ | H | H | O | 4 | 4-chloro-6-trifluoromethylpyrimidin-2-yl | |
| 44 | CH₃ | CH₃ | H | H | O | 4 | 4-methyl-5-trifluoromethylpyrimidin-2-yl | m.p. 168–170 |
| 45 | CH₃ | CH₃ | H | H | O | 4 | 4-methylamino-6-trifluoromethylpyrimidin-2-yl | |
| 46 | CH₃ | CH₃ | H | H | O | 4 | 4-trifluoromethylpyrimidin-2-yl | m.p. 191–192 |
| 47 | CH₃ | CH₃ | H | H | O | 4 | 2-trifluoromethyl-6-chloropyrimidin-4-yl | m.p. 173–175 |
| 48 | CH₃ | CH₃ | H | H | O | 4 | 2-trifluoromethylpyrimidin-4-yl | m.p. 224–225 |
| 49 | CH₃ | CH₃ | H | H | O | 4 | 2-trifluoromethyl-6-methylpyrimidin-4-yl | m.p. 209–210 |
| 50 | CH₃ | CH₃ | H | H | S | 4 | 4,6-dimethylpyrimidin-2-yl | |
| 51 | CH₃ | CH₃ | H | H | S | 4 | 4-chloropyrimidin-2-yl | |
| 52 | CH₃ | CH₃ | H | H | S | 4 | 6-chloropyrimidin-4-yl | |
| 53 | CH₃ | CH₃ | H | H | S | 4 | 2-isopropyl-6-methylpyrimidin-4-yl | |
| 54 | CH₃ | CH₃ | H | H | S | 4 | 2-methylthio-6-methylpyrimidin-4-yl | |
| 55 | CH₃ | CH₃ | H | H | S | 4 | 4-chloro-6-trifluoromethylpyrimidin-2-yl | |
| 56 | CH₃ | CH₃ | H | H | S | 4 | 4-methyl-6-trifluoromethylpyrimidin-2-yl | m.p. 195–197 |
| 57 | CH₃ | CH₃ | H | H | S | 4 | 2-trifluoromethylpyrimidin-4-yl | m.p. 173–174 |
| 58 | CH₃ | CH₃ | H | H | S | 4 | 2-trifluoromethyl-6-methoxypyrimidin-4-yl | |
| 59 | CH₃ | CH₃ | 4-OCH₃ | H | S | 3 | 6-trifluoromethylpyrimidin-4-yl | m.p. 195–196 |
| 60 | CH₃ | CH₃ | 4-OCH₃ | H | S | 3 | 6-chloropyrimidin-4-yl | |
| 61 | CH₃ | CH₃ | 3-OCH₃ | H | S | 4 | 4-trifluoromethylpyrimidin-2-yl | m.p. 180–184 |
| 62 | CH₃ | CH₃ | 2-CH₃ | H | S | 4 | 2,6-dimethylpyrimidin-4-yl | |
| 63 | CH₃ | CH₃ | 2-CH₃ | 6-CH₃ | S | 4 | 4-chloropyrimidin-2-yl | |
| 64 | OCH₃ | CH₃ | H | H | O | 4 | 6-chloropyrimidin-4-yl | |
| 65 | OCH₃ | CH₃ | H | H | O | 4 | 2-methylthiopyrimidin-4-yl | |
| 66 | OCH₃ | CH₃ | H | H | O | 4 | 6-trifluoromethylpyrimidin-4-yl | |
| 67 | CH₃ | CH₃ | H | H | O | 4 | 5-trifluoromethylpyrimidin-2-yl | |
| 68 | CH₂—CH=CH₂ | CH₃ | H | H | O | 4 | 6-chloropyrimidin-4-yl | |
| 69 | cyclopropyl | CH₃ | H | H | O | 4 | 6-methylpyrimidin-4-yl | |
| 70 | C₂H₅ | CH₃ | H | H | O | 4 | 4-trifluoromethylpyrimidin-2-yl | |
| 71 | CH₃ | CH₃ | 2-CH₃ | H | O | 4 | 4-chloropyrimidin-2-yl | |
| 72 | CH₃ | CH₃ | 2-isoC₃H₇ | H | O | 4 | 6-trifluoromethylpyrimidin-4-yl | m.p. 149–151 |
| 73 | CH₃ | CH₃ | 2-CH₃ | 6-CH₃ | O | 4 | 2-trifluoromethylpyrimidin-4-yl | m.p. 196–197 |
| 74 | CH₃ | CH₃ | 4-OCH₃ | H | O | 3 | 2-methyl-6-chloropyrimidin-4-yl | |
| 75 | CH₃ | CH₃ | 4-OCH₃ | H | O | 3 | 6-trifluoromethylpyrimidin-4-yl | m.p. 196–197 |
| 76 | CH₃ | CH₃ | 3-OCH₃ | H | O | 4 | 2-trifluoromethylpyrimidin-4-yl | m.p. 218–220 |
| 77 | CH₃ | CH₃ | 3-OCH₃ | H | O | 4 | 2-methyl-6-chloropyrimidin-4-yl | m.p. 204–208 |
| 78 | CH₃ | CH₃ | H | H | O | 4 | 2-methylthio-6-trifluoromethylpyrimidin-4-yl | m.p. 161–163 |
| 79 | CH₃ | CH₃ | H | H | O | 4 | 2-Methyl-5-trifluoromethylpyrimidin-4-yl | m.p. 171–173 |
| 80 | CH₃ | CH₃ | 2-isoC₃H₇ | H | S | 4 | 6-trimethylpyrimidin-4-yl | m.p. 157–158 |
| 81 | OCH₃ | CH₃ | 4-OCH₃ | H | O | 3 | 6-trifluoromethylpyrimidin-4-yl | |
| 82 | CH₂—CH=CH₂ | CH₃ | H | H | O | 4 | 5-trifluoromethylpyrimidin-2-yl | |
| 83 | OCH₃ | CH₃ | H | H | O | 4 | 4-trifluoromethylpyrimidin-2-yl | |
| 84 | CH₃ | CH₃ | 2-CH₃ | 6-CH₃ | S | 4 | trifluoromethylpyrimidin-4-yl | m.p. 179–181 |
| 85 | CH₃ | CH₃ | H | H | O | 4 | 2-trifluoromethyl-6-methoxypyrimidin-4-yl | |
| 86 | CH₃ | CH₃ | H | H | O | 4 | 2-trifluoromethyl-6-methylthiopyrimidin-4-yl | |
| 87 | CH₃ | CH₃ | H | H | O | 4 | 2-trifluoromethyl-6-methylaminopyrimidin-4-yl | |
| 88 | CH₃ | CH₃ | H | H | O | 4 | 2-trifluoromethyl-6-dimethylamino-pyrimidin-4-yl | |
| 89 | CH₃ | CH₃ | H | H | S | 4 | 2-trifluoromethyl-6-chloropyrimidin-4-yl | |

TABLE 1-continued

Compounds of the formula

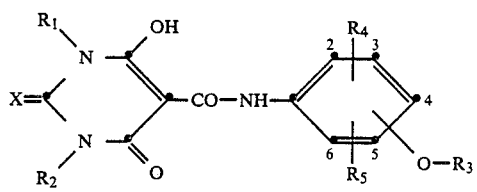

| Comp. | R₁ | R₂ | R₄ | R₅ | X | Position —O—R₃ | R₃ | Physical data [°C.] |
|---|---|---|---|---|---|---|---|---|
| 90 | cyclopropyl | CH₃ | H | H | O | 4 | 4-trifluoromethylpyrimidin-2-yl | |
| 91 | CH₃ | CH₃ | H | H | S | 4 | 4-methoxy-6-methyl-1,3,5-triazin-2-yl | |
| 92 | CH₃ | CH₃ | H | H | O | 4 | 4-chloro-6-methyl-1,3,5-triazin-2-yl | |
| 94 | CH₃ | CH₃ | H | H | O | 4 | 4,6-dichloro-1,3,5-triazin-2-yl | |
| 95 | CH₃ | CH₃ | H | H | O | 4 | 4-ethoxy-6-methoxy-1,3,5-triazin-2-yl | |
| 96 | CH₃ | CH₃ | H | H | O | 4 | 4-methyl-1,3,5-triazin-2-yl | |
| 97 | CH₃ | CH₃ | H | H | O | 4 | 4-chloro-6-trifluoromethyl-1,3,5-triazin-2-yl | |
| 98 | CH₃ | CH₃ | H | H | O | 4 | 4-chloromethyl-6-methyl-1,3,5-triazin-2-yl | |
| 99 | CH₃ | CH₃ | H | H | O | 4 | 4-methyl-6-tert-butyl-1,3,5-triazin-2-yl | |
| 100 | CH₃ | CH₃ | H | H | O | 4 | 4-chloromethyl-6-methoxy-1,3,5-triazin-2-yl | |
| 101 | CH₃ | CH₃ | H | H | O | 4 | 4-methylthio-1,3,5-triazin-2-yl | |
| 102 | CH₃ | CH₃ | H | H | O | 4 | 4-methoxy-6-methyl-1,3,5-triazin-2-yl | |
| 103 | OCH₃ | CH₃ | H | H | O | 4 | 4-ethyl-6-methoxy-1,3,5-triazin-2-yl | |
| 104 | CH₃ | CH₃ | H | H | O | 4 | 4-methyl-6-trifluoromethyl-1,3,5-triazin-2-yl | |
| 105 | CH₃ | CH₃ | H | H | O | 4 | 4-methoxy-5-methyl-1,2,4-triazin-3-yl | |
| 106 | CH₃ | CH₃ | H | H | O | 4 | 4-chloro-6-methoxy-1,3,5-triazin-2-yl | |
| 107 | CH₃ | CH₃ | H | H | O | 4 | 4,6-dimethoxy-1,3,5-triazin-2-yl | |
| 108 | CH₃ | CH₃ | H | H | O | 4 | 4-methoxy-1,3,5-triazin-2-yl | |
| 109 | CH₃ | CH₃ | H | H | O | 3 | 4-methoxy-6-methyl-1,3,5-triazin-2-yl | |
| 110 | CH₃ | CH₃ | H | H | O | 4 | 4-chloro-1,3,5-triazin-2-yl | |
| 111 | CH₃ | CH₃ | H | H | O | 4 | 4-methoxy-6-methylthio-1,3,5-triazin-2-yl | |
| 112 | CH₃ | CH₃ | H | H | S | 4 | 3,5-dichloro-1,2,4-triazin-6-yl | |
| 113 | CH₃ | CH₃ | H | H | O | 4 | 4-cyclopropyl-6-methoxy-1,3,5-triazin-2-yl | |
| 114 | CH₃ | CH₃ | H | H | O | 4 | 4-methyl-6-methylthio-1,3,5-triazin-2-yl | |
| 115 | CH₃ | CH₃ | H | H | O | 4 | 4-ethyl-6-methyl-1,3,5-triazin-2-yl | |
| 116 | CH₃ | CH₃ | H | H | O | 4 | 4-dimethylamino-6-(2,2,2-trifluoroethoxy)-1,3,5-triazin-2-yl | |
| 117 | CH₃ | CH₃ | H | H | O | 4 | 4-isopropyl-6-methyl-1,3,5-triazin-2-yl | |
| 118 | CH₃ | CH₃ | H | H | O | 4 | 4-methoxy-5-trifluoromethyl-1,3,5-triazin-2-yl | |
| 119 | OCH₃ | CH₃ | H | H | O | 4 | 4-methoxy-6-methyl-1,3,5-triazin-2-yl | |
| 120 | CH₃ | CH₃ | H | H | O | 4 | 4-allyl-6-methyl-1,3,5-triazin-2-yl | |
| 121 | CH₃ | CH₃ | H | H | O | 4 | 4-methylamino-6-trifluoromethyl-1,3,5-triazin-2-yl | |
| 122 | CH₃ | CH₃ | 3-OCH₃ | H | O | 4 | 4,6-dimethyl-1,3,5-triazin-2-yl | |
| 123 | CH₃ | CH₃ | H | H | O | 4 | 4-trifluoromethyl-1,3,5-triazin-2-yl | |
| 124 | CH₃ | CH₃ | H | H | O | 4 | 4,6-dimethyl-1,3,5-triazin-2-yl | |
| 125 | CH₃ | CH₃ | H | H | O | 4 | 4-methylamino-6-methoxy-1,3,5-triazin-2-yl | |
| 126 | CH₃ | CH₃ | H | H | O | 4 | 3,6-dimethyl-1,2,4-triazin-5-yl | |
| 127 | CH₃ | CH₃ | H | H | O | 4 | 4-(difluoromethylthio)-6-methyl-1,3,5-triazin-2-yl | |
| 128 | CH₃ | CH₃ | H | H | O | 4 | 4-methylamino-6-tert-butyl-1,3,5-triazin-2-yl | |
| 129 | CH₃ | CH₃ | H | H | O | 4 | 4-isopropyloxy-6-methoxy-1,3,5-triazin-2-yl | |
| 130 | CH₃ | CH₃ | H | H | O | 4 | 4-cyclopropyl-6-methyl-amino-1,3,5-triazin-2-yl | |
| 131 | CH₃ | CH₃ | H | H | O | 4 | 4-chloro-6-methylthio-1,3,5-triazin-2-yl | |
| 132 | CH₃ | CH₃ | H | H | O | 4 | 3,5-dichloro-1,2,4-triazin-6-yl | |
| 133 | CH₃ | CH₃ | H | H | O | 4 | 4-allyl-1,3,5-triazin-2-yl | |
| 134 | CH₃ | CH₃ | H | H | O | 4 | 4-methoxy-6-(2,2,2-trifluoroethoxy)-1,3,5-triazin-2-yl | |
| 135 | CH₃ | CH₃ | H | H | O | 4 | 4-fluoromethyl-6-methoxy-1,3,5-triazin-2-yl | |
| 136 | CH₃ | CH₃ | H | H | S | 4 | 2,6-dimethylpyrimidin-4-yl | m.p. 205–206 |
| 137 | CH₃ | CH₃ | H | H | O | 4 | 4-chloro-6-ethylamino-1,3,5-triazin-2-yl | |
| 138 | CH₃ | CH₃ | H | H | O | 4 | 4,6-bis(methylthio)-1,3,5-triazine-2-yl | |
| 139 | CH₃ | CH₃ | H | H | O | 4 | 5-chloropyrimidin-2-yl | m.p. 212–213 |
| 140 | CH₃ | CH₃ | 3-OCH₃ | H | O | 4 | 5-methyl-4-trifluoromethylpyrimidin-2-yl | m.p. 200–201 |
| 141 | CH₃ | CH₃ | 2-CH₃ | 6-CH₃ | O | 4 | pyrazin-2-yl | m.p. >240 |
| 142 | CH₃ | CH₃ | H | H | O | 3 | 6-chloropyridazin-3-yl | |
| 143 | CH₃ | CH₃ | H | H | O | 4 | 2-phenyl-6-chloropyrimidin-4-yl | |
| 144 | CH₃ | CH₃ | H | H | O | 4 | 5-phenyl-4-trifluoromethylpyrimidin-2-yl | m.p. 180–181 |
| 145 | CH₃ | CH₃ | 4-OCH₃ | H | O | 3 | 5-methyl-4-trifluoromethylpyrimidin-2-yl | m.p. 170–172 |
| 146 | CH₃ | CH₃ | 3-C₂H₅ | H | O | 4 | 6-methyl-4-trifluoromethylpyrimidin-2-yl | |
| 147 | CH₃ | CH₃ | 2-n-C₃H₇ | H | S | 4 | 6-methyl-4-trifluoromethylpyrimidin-2-yl | |
| 148 | OCH₃ | CH₃ | H | H | O | 4 | 5-chloropyrimidin-2-yl | m.p. 192–194 |
| 149 | CH₃ | CH₃ | H | H | S | 4 | 2-methylthio-6-trifluoromethylpyrimidin-4-yl | |
| 150 | CH₃ | CH₃ | H | H | O | 4 | 2,6-bis(trifluoromethyl)pyrimidin-4-yl | m.p. 159–160 |
| 151 | CH₃ | CH₃ | 2-n-C₃H₇ | H | O | 4 | 6-chloro-2-trifluoromethylpyrimidin-4-yl | |
| 152 | CH₃ | CH₃ | H | H | S | 4 | 6-methyl-2-trifluoromethylpyrimidin-4-yl | |
| 153 | CH₃ | CH₃ | H | H | O | 4 | 6-chloro-1-oxypyridazin-3-yl | m.p. 267–269 |
| 154 | CH₃ | CH₃ | 4-OC₂H₅ | H | S | 3 | 6-trifluoromethylpyrimidin-4-yl | |

TABLE 1-continued
Compounds of the formula

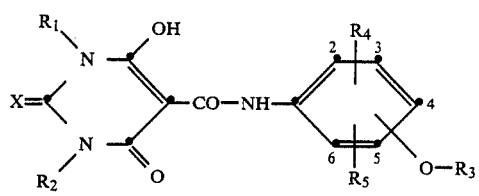

| Comp. | R₁ | R₂ | R₄ | R₅ | X | Position —O—R₃ | R₃ | Physical data [°C.] |
|---|---|---|---|---|---|---|---|---|
| 155 | CH₂—CH=CH₂ | CH₃ | H | H | O | 4 | 6-trifluoromethylpyrimidin-4-yl | |
| 156 | C₂H₅ | CH₃ | H | H | S | 4 | 6-trifluoromethylpyrimidin-4-yl | |
| 157 | C₂H₅ | CH₃ | H | H | O | 4 | 6-methyl-2-trifluoromethyl-pyrimidin-4-yl | |
| 158 | CH₃ | CH₃ | H | H | S | 4 | 5-trifluoromethylpyrimidin-2-yl | |
| 159 | CH₂—CH=CH₂ | CH₃ | H | H | S | 4 | 5-trifluoromethylpyrimidin-2-yl | |
| 160 | C₂H₅ | CH₃ | H | H | O | 4 | 5-trifluoromethylpyrimidin-2-yl | |
| 161 | CH₃ | CH₃ | 4-OC₂H₅ | H | S | 3 | 5-trifluoromethylpyrimidin-2-yl | |
| 162 | CH₃ | CH₃ | H | H | S | 4 | 4-chloro-6-trifluoromethyl-1,3,5-triazin-2-yl | |
| 163 | CH₃ | CH₃ | H | H | S | 4 | 4-trifluoromethyl-1,3,5-triazin-2-yl | |
| 164 | iso-C₃H₇ | CH₃ | H | H | O | 4 | 4-trifluoromethylpyrimidin-2-yl | |
| 165 | iso-C₃H₇ | CH₃ | H | H | S | 4 | 4-trifluoromethylpyrimidin-2-yl | |
| 166 | CH₃ | CH₃ | H | H | S | 4 | 4-trifluoromethylpyrimidin-2-yl | |
| 167 | CH₂—CH=CH₂ | CH₃ | H | H | S | 4 | 4-trifluoromethylpyrimidin-2-yl | |
| 168 | cyclopropyl | CH₃ | H | H | S | 4 | 4-trifluoromethylpyrimidin-2-yl | |
| 169 | CH₃ | CH₃ | 2-OCH₃ | H | O | 4 | 4-trifluoromethylpyrimidin-2-yl | |
| 170 | CH₃ | CH₃ | 3-OC₂H₅ | H | S | 4 | 6-trifluoromethylpyrimidin-4-yl | |
| 171 | CH₃ | CH₃ | 4-OC₂H₅ | H | S | 3 | 6-trifluoromethylpyrimidin-4-yl | |
| 172 | CH₃ | CH₃ | 4-CH₃ | H | O | 3 | 6-trifluoromethylpyrimidin-4-yl | |
| 173 | CH₃ | CH₃ | 4-CH₃ | H | O | 2 | 6-trifluoromethylpyrimidin-4-yl | |
| 174 | CH₃ | CH₃ | 4-CH₃ | H | S | 2 | 6-trifluoromethylpyrimidin-4-yl | |
| 175 | CH₂—CH=CH₂ | CH₃ | 4-CH₃ | H | O | 2 | 6-trifluoromethylpyrimidin-4-yl | |
| 176 | iso-C₃H₇ | CH₃ | 4-CH₃ | H | O | 2 | 6-trifluoromethylpyrimidin-4-yl | |
| 177 | CH₃ | CH₃ | 2-OCH₃ | H | O | 4 | 6-trifluoromethylpyrimidin-4-yl | |
| 178 | CH₂—CH=CH₂ | CH₃ | H | H | O | 4 | 2-methyl-6-trifluoromethylpyrimidin-4-yl | |
| 179 | C₂H₅ | CH₃ | H | H | O | 4 | 2-methyl-6-trifluoromethylpyrimidin-4-yl | |
| 180 | CH₃ | CH₃ | H | H | S | 4 | 2-methyl-6-trifluoromethylpyrimidin-4-yl | |
| 181 | CH₃ | CH₃ | 4-CH₃ | H | O | 3 | 2-methyl-6-trifluoromethylpyrimidin-4-yl | |
| 182 | CH₃ | CH₃ | 4-CH₃ | H | S | 3 | 2-methyl-6-trifluoromethylpyrimidin-4-yl | |
| 183 | CH₂—CH=CH₂ | CH₃ | 4-CH₃ | H | O | 3 | 2-methyl-6-trifluoromethylpyrimidin-4-yl | |
| 184 | iso-C₃H₇ | CH₃ | 4-CH₃ | H | S | 3 | 2-methyl-6-trifluoromethylpyrimidin-4-yl | |
| 185 | CH₃ | CH₃ | H | H | O | 4 | 2-isopropyl-6-trifluoromethylpyrimidin-4-yl | |
| 186 | CH₃ | CH₃ | 2-CH₃ | 6-CH₃ | S | 4 | 2-isopropyl-6-trifluoromethylpyrimidin-4-yl | |
| 187 | CH₃ | CH₃ | H | H | O | 4 | 2-tert-butyl-6-trifluoromethylpyrimidin-4-yl | |
| 188 | CH₃ | CH₃ | H | H | S | 4 | 2-tert-butyl-6-trifluoromethylpyrimidin-4-yl | |
| 189 | CH₃ | CH₃ | H | H | O | 4 | 2-cyclopropyl-6-trifluoromethylpyrimidin-4-yl | |
| 190 | CH₃ | CH₃ | H | H | S | 4 | 2-cyclopropyl-6-trifluoromethylpyrimidin-4-yl | |

TABLE 2
Compounds of formula III

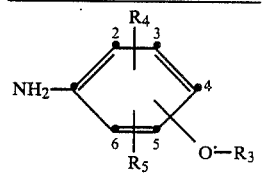

| Comp. | R₄ | R₅ | Position —O—R₃ | R₃ | Physical data [°C.] |
|---|---|---|---|---|---|
| 2.1 | H | H | 4 | 3-methylpyrazin-2-yl | m.p. 108–109 |
| 2.2 | H | H | 4 | 3-chloropyrazin-2-yl | m.p. 130–131 |
| 2.3 | H | H | 4 | 6-chloroquinoxalin-2-yl | m.p. 107–112 |
| 2.4 | H | H | 4 | pyrimidin-2-yl | m.p. 125–129 |
| 2.5 | H | H | 4 | 4,6-dimethylpyrimidin-2-yl | m.p. 92–96 |
| 2.6 | H | H | 4 | 4-chloropyrimidin-2-yl | oil |
| 2.7 | H | H | 4 | 6-chloropyrimidin-4-yl | oil |
| 2.8 | H | H | 4 | quinolin-2-yl | |
| 2.9 | H | H | 4 | 6-chloropyridazin-3-yl | |
| 2.10 | H | H | 4 | 6-methoxypyridazin-3-yl | |
| 2.11 | H | H | 4 | 2-isopropyl-6-methylpyrimidin-4-yl | |
| 2.12 | H | H | 4 | 2-methylthio-6-methylpyrimidin-4-yl | oil |
| 2.13 | H | H | 4 | 2-tert-butyl-6-chloro-pyrimidin-4-yl | oil |
| 2.14 | H | H | 4 | 2-methyl-6-chloropyrimidin-4-yl | |
| 2.15 | H | H | 4 | 2-methylthio-5-phenyl-6-chloropyrimidin-4-yl | |
| 2.16 | H | H | 4 | 2-methylthiopyrimidin-4-yl | |

TABLE 2-continued

Compounds of formula III

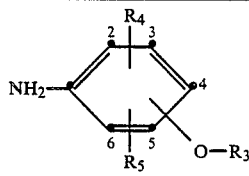

| Comp. | R₄ | R₅ | Position —O—R₃ | R₃ | Physical data [°C.] |
|---|---|---|---|---|---|
| 2.17 | H | H | 4 | 2,6-dimethylpyrimidin-4-yl | |
| 2.18 | H | H | 4 | 4-methylpyrimidin-2-yl | |
| 2.19 | H | H | 4 | 4-chloro-6-dimethylamino-1,3,5-triazin-2-yl | |
| 2.20 | H | H | 4 | 6-trifluoromethylpyrimidin-4-yl | |
| 2.21 | H | H | 4 | 4-methyl-6-trifluoromethylpyrimidin-2-yl | |
| 2.22 | H | H | 4 | 4-trifluoromethylpyrimidin-2-yl | |
| 2.23 | H | H | 4 | 2-trifluoromethyl-6-chloropyrimidin-4-yl | |
| 2.24 | H | H | 4 | 2-trifluoromethylpyrimidin-4-yl | |
| 2.25 | H | H | 4 | 2-trifluoromethyl-6-methylpyrimidin-4-yl | |
| 2.26 | 4-OCH₃ | H | 3 | 6-trifluoromethylpyrimidin-4-yl | |
| 2.27 | 3-OCH₃ | H | 4 | 4-trifluoromethylpyrimidin-2-yl | |
| 2.28 | 2-isoC₃H₇ | H | 4 | 6-trifluoromethylpyrimidin-4-yl | |
| 2.29 | 2-CH₃ | 6-CH₃ | 4 | 2-trifluoromethylpyrimidin-4-yl | |
| 2.30 | 3-OCH₃ | H | 4 | 2-trifluoromethylpyrimidin-4-yl | |
| 2.31 | 3-OCH₃ | H | 4 | 2-methyl-6-chloropyrimidin-4-yl | |
| 2.32 | H | H | 4 | 2-methylthio-6-trifluoromethylpyrimidin-4-yl | |
| 2.33 | H | H | 4 | 2-methyl-6-trifluoromethylpyrimidin-4-yl | |
| 2.34 | H | H | 4 | 5-chloropyrimidin-2-yl | |
| 2.35 | 3-OCH₃ | H | 4 | 5-methyl-4-trifluoromethylpyrimidin-2-yl | |
| 2.36 | 2-CH₃ | 6-CH₃ | 4 | pyrazin-2-yl | |
| 2.37 | H | H | H | 5-phenyl-4-trifluoromethylpyrimidin-2-yl | |
| 2.38 | 4-OCH₃ | H | 3 | 5-methyl-4-trifluoromethylpyrimidin-2-yl | |
| 2.39 | H | H | 4 | 2,6-bis(trifluoromethyl)pyrimidin-4-yl | |
| 2.40 | H | H | 4 | 6-chloro-1-oxypyridazin-3-yl | |

3. FORMULATION EXAMPLES (throughout, percentages are by weight)

| 3.1. Emulsifiable concentrates | (a) | (b) | (c) |
|---|---|---|---|
| a compound of Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 3.2. Solutions | (a) | (b) | (c) | (d) |
|---|---|---|---|---|
| a compound of Table 1 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| 3.3. Granulates | (a) | (b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo. Such granulates can be mixed with the cattle feed.

| 3.4. Dusts | (a) | (b) |
|---|---|---|
| compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 3.5. Wettable powders | (a) | (b) | (c) |
|---|---|---|---|
| a compound of Table 1 | 25% | 50% | 75% |
| sodium lignosulfonate | 5% | 5% | — |
| oleic acid | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 3.6. Emulsifiable concentrate | (a) | (b) | (c) |
|---|---|---|---|
| a compound of Table 1 | 10% | 8% | 60% |
| octylphenol polyethylene glycol ether (4–5 moles of ethylene oxide) | 3% | 3% | 2% |
| calcium dodecylbenzenesulfonate | 3% | 4% | 4% |

| 3.6. Emulsifiable concentrate | (a) | (b) | (c) |
|---|---|---|---|
| castor oil polyglcol ether (35 moles of ethylene oxide) | 4% | 5% | 4% |
| cyclohexanone | 30% | 40% | 15% |
| xylene mixture | 50% | 40% | 15% |

Emulsions of any required concentration can be obtained from this concentrate by dilution with water.

| 3.7. Dust | (a) | (b) |
|---|---|---|
| a compound of Table 1 | 5% | 8% |
| talcum | 95% | — |
| kaolin | — | 92% |

Ready-for-use dusts are obtained by mixing the active ingredient with the carrier, and grinding the mixture in a suitable mill.

| 3.8. Granulate | |
|---|---|
| a compound of Table 1 | 10% |
| sodium lignosulfonate | 2% |
| carboxymethylcellulsoe | 1% |
| kaolin | 87% |

The active ingredient is mixed and ground with the adjuvants, and the mixture is subsequently moistened with water. The mixture is extruded and then dried in a stream of air.

| 3.9. Granulate | |
|---|---|
| a compound of Table 1 | 3% |
| polyethlene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 3.10. Suspension concentrate | |
|---|---|
| a compound of Table 1 | 40% |
| ethylene glycol | 10% |
| nonylphenol polyethylene glycol (15 moles of ethlene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

| 3.11. Pellets or boluses | | |
|---|---|---|
| I | a compound of Table I | 33.0% |
| | methyl cellulose | 0.80% |
| | highly dispersed silicic acid | 0.80% |
| | maize starch | 8.40% |
| II | crystalline lactose | 22.50% |
| | maize starch | 17.00% |
| | microcrystalline cellulose | 16.50% |
| | magnesium stearate | 1.00% |

| 3.11. Pellets or boluses | |
|---|---|
| I | The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12 M sieve and the granulate is dried. |
| II | All 4 adjuvants are thoroughly mixed. |
| III | Phases I and II are mixed and compressed to pellets or boluses. |

4. BIOLOGICAL EXAMPLE

The following test procedure is employed to demonstrate the anthelmintic activity of the compounds of formula I:

EXAMPLE 4.1

Trial with sheep infected with nematodes such as *Haemonchus contortus* and *Trichostrongylus colubriformis*

The test compound is administered in the form of a suspension with a stomach probe or by intrarumenal injection to sheep which have been artificially infected beforehand with nematodes such as *Haemonchus contortus* and *Trichostrongylus colubriformis*. One to three animals are used for each trial and for each dose. Each sheep is treated with only a single dose. A first evaluation is made by comparing the number of worm eggs excreted in the faeces of the sheep before and after treatment. The sheep are slaughtered and dissected 7 to 10 days after treatment. Evaluation is made by counting the number of worms remaining in the intestine after treatment. Untreated sheep infected simultaneously and in the same manner are used as controls.

Compared with untreated and infected control groups, nematode infestation is reduced by 90% or more in sheep which are treated with a suspension formulation of a compound of Table I at a dose of 20 mg/kg of body weight or less. For example compounds 1, 2, 9 and 76 reduce nematode infestation by at least 90% when applied at a dose of 20 mg/kg of body weight. Moreover, compounds 42, 44, 46, 48, 49, 56, 57, 59, 61, 72, 73, 79, 80, 84, 139, 140, 144 and 153 reduce nematode infestation by 90% or more when applied at a dose of 10 mg/kg of body weight.

What is claimed is:

1. A 5-phenylcarbamoylbarbituric acid compound of the formula

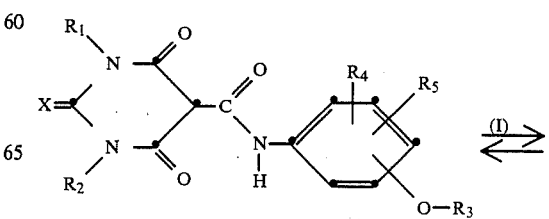

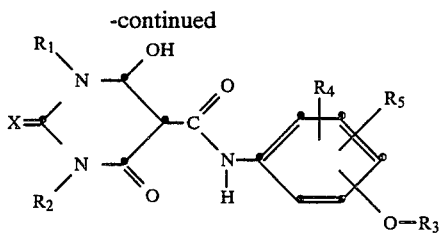

wherein

R₁ is $C_1$-$C_4$alkyl, $C_1$-$C_3$alkoxy, allyl or $C_3$-$C_6$cycloalkyl,

R₂ is $C_1$-$C_4$alkyl or allyl,

R₃ is a 6-membered aromatic ring which has 2 or 3 ring nitrogen atoms or is a 6-membered aromatic ring which is fused to a benzene ring and which has 1 to 3 ring nitrogen atoms, either of which is unsubstituted or substituted by $C_1$-$C_4$alkyl, $C_1$-$C_4$haloalkyl, alkoxyalkyl having 2-4 carbon atom, $C_1$-$C_4$alkoxy, $C_1$-$C_4$haloalkoxy, $C_1$-$C_4$alkylthio, $C_1$-$C_4$haloalkylthio, $C_1$-$C_3$alkylamino, di($C_1$-$C_3$alkyl)amino, allyl, propargyl, halogen, nitro, cyano, $C_3$-$C_6$cycloalkyl or phenyl, R₄ and R₅ are each independently of the other hydrogen, $C_1$-$C_4$alkyl, $C_1$-$C_4$alkoxy or $C_1$-$C_3$haloalkyl and X is an oxygen or sulfur atom, or a tautomer, salt that is non-toxic to the target host or N oxide thereof.

2. A compound according to claim 1, or a tautomer or salt that is non-toxic to the target host of such compound.

3. A compound according to claim 2, wherein R₃ is a cyclic group selected from the group consisting of

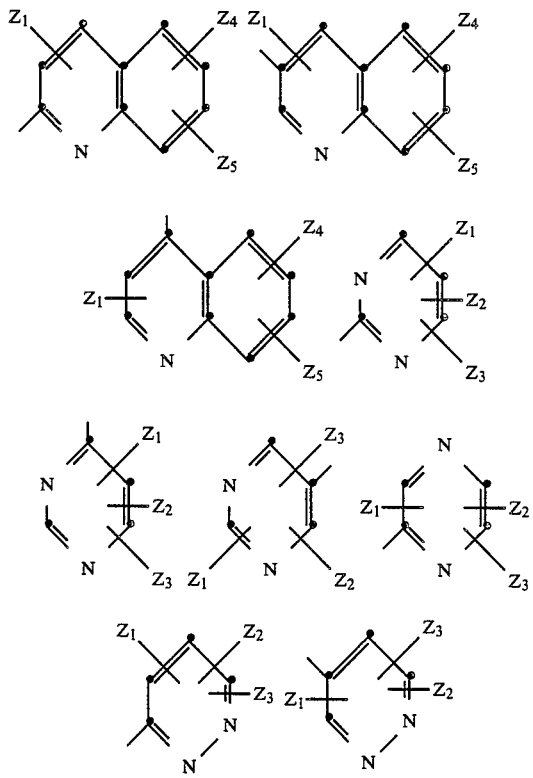

in which formulae each of $Z_1$, $Z_2$, $Z_3$, $Z_4$ and $Z_5$ independently of one another is hydrogen, $C_1$-$C_4$alkyl, $C_1$-$C_4$haloalkyl, alkoxyalkyl containing a total of 2 to 4 carbon atoms, $C_1$-$C_4$alkoxy, $C_1$-$C_4$haloalkoxy, $C_1$-$C_4$alkylthio, $C_1$-$C_4$haloalkylthio, $C_1$-$C_3$alkylamino, di($C_1$-$C_3$alkyl)amino, allyl, propargyl, halogen, nitro, cyano, $C_3$-$C_6$cycloalkyl or phenyl, $Z_1$, $Z_2$ and $Z_3$ being on the heteroaromatic ring, and $Z_4$ and $Z_5$ being on the fused aromatic ring.

4. A compound according to claim 1, wherein R₁ is $C_1$-$C_4$alkyl, $C_1$-$C_3$alkoxy, allyl or $C_3$-$C_6$cycloalkyl, R₂ is $C_1$-$C_4$alkyl, R₃ is a pyrazinyl, pyrimidinyl, pyridazinyl, triazinyl, quinoxalinyl or quinolinyl group, each of which is bound through a carbon atom and is unsubstituted or substituted by one to three substituents selected from the group consisting of $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_3$alkylamino, di($C_1$-$C_3$alkyl)amino, allyl, halogen, $C_3$-$C_6$-cycloalkyl and phenyl, R₄ is hydrogen, $C_1$-$C_4$alkyl or $C_1$-$C_4$alkoxy, R₅ is hydrogen or $C_1$-$C_4$alkyl and X is an oxygen or sulfur atom.

5. A compound according to claim 4, wherein R₁ is $C_1$-$C_4$alkyl, allyl, cyclopropyl or $C_1$-$C_3$alkoxy, R₂ is $C_1$-$C_4$alkyl, R₃ is a pyrazinyl, pyrimidinyl, pyridazinyl, triazinyl, quinoxalinyl or quinolinyl group, each of which is bound through a carbon atom and is unsubstituted or substituted by one to three substituents selected from the group consisting of $C_1$-$C_4$alkyl, $C_1$-$C_4$haloalkyl, $C_1$-$C_4$alkoxy, $C_1$-$C_4$alkylthio, di($C_1$-$C_3$alkyl)amino, halogen and phenyl, R₄ is hydrogen, $C_1$-$C_4$alkyl or $C_1$-$C_4$alkoxy, R₅ is hydrogen or $C_1$-$C_4$alkyl and X is an oxygen or sulfur atom.

6. A compound according to claim 1, wherein R₁ is $C_1$-$C_4$alkyl, methoxy, allyl or cyclopropyl, R₂ is methyl, R₃ is a pyrazinyl, pyridazinyl, triazinyl, pyrimidinyl, quinoxalinyl, quinolyl or quinazolinyl group, each of which is unsubstituted or substituted by one to three substituents selected from the group consisting of $C_1$-$C_4$alkyl, methoxy, methylamino, dimethylamino, methylthio, trifluoromethyl, halogen and phenyl, $R_4$ is hydrogen, $C_1$-$C_4$alkyl or methoxy, $R_5$ is hydrogen or methyl and X is an oxygen or sulfur atom.

7. A compound according to claim 5, wherein $R_1$ is $C_1$-$C_4$alkyl, allyl, cyclopropyl or methoxy, $R_2$ is methyl, $R_3$ is a pyrimidinyl, pyrazinyl or pyridazinyl group, each of which is bound through a carbon atom and is unsubstituted or substituted by one to three substituents selected from the group consisting of $C_1$-$C_4$alkyl, trifluoromethyl, methoxy, methylthio, chlorine and phenyl, $R_4$ is hydrogen, $C_1$-$C_4$alkyl or $C_1$-$C_4$alkoxy, $R_5$ is hydrogen or $C_1$-$C_4$alkyl and X is an oxygen or sulfur atom and the molecule fragment —$OR_3$ is in the meta- or para-position to the nitrogen atom of the carbamoyl group.

8. A compound according to claim 5, wherein $R_1$ is methyl or methoxy, $R_2$ is methyl, $R_3$ is a pyrimidinyl ring which is bound through a carbon atom and is unsubstituted or substituted by one or two substituents selected from the group consisting of $C_1$-$C_4$alkyl, $C_1$-$C_4$haloalkyl, halogen and phenyl, $R_4$ is hydrogen, $C_1$-$C_4$alkyl or $C_1$-$C_4$alkoxy, $R_5$ is hydrogen or methyl and X is an oxygen or sulfur atom and the molecule fragment —$OR_3$ is in the meta- or para-position to the nitrogen atom of the carbamoyl group.

9. A compound according to claim 8, wherein $R_1$ is methyl, $R_2$ is methyl, $R_3$ is a pyrimidinyl ring which is bound through a carbon atom and is substituted by one or two substituents selected from the group consisting of methyl, trifluoromethyl, chlorine and phenyl, $R_4$ is hydrogen, methyl, isopropyl, methoxy or ethoxy, $R_5$ is hydrogen or methyl and X is an oxygen or sulfur atom and the molecule fragment —$OR_3$ is in the meta- or para-position to the nitrogen atom of the carbamoyl group.

10. A compound according to claim 9, wherein $R_1$ is methyl, $R_2$ is methyl, $R_3$ is a pyrimidinyl ring which is bound through a carbon atom and is substituted by one trifluoromethyl group or is substituted by not more than two substituents, namely by one trifluoromethyl group and by one further substituent selected from the group consisting of methyl, trifluoromethyl, chlorine and phenyl, $R_4$ is hydrogen, methyl, isopropyl or methoxy, $R_5$ is hydrogen or methyl and X is an oxygen or sulfur atom and the molecule fragment —$OR_3$ is in the para-position to the nitrogen atom of the carbamoyl group.

11. A compound according to claim 1 selected from the group consisting of 1,3-dimethyl-5-[4-(6-chloro-1-oxypyridazin-3-yloxy)-phenylcarbamoyl]barbituric acid, 1,3-dimethyl-5-[4-(3-methylpyrazin-2-yloxy)phenylcarbamoyl]barbituric acid, 1,3-dimethyl-5-[4-(3-chloropyrazin-2-yloxy)phenylcarbamoyl]barbituric acid, 1,3-dimethyl-5-[4-(3-methylpyrazin-2-yloxy)phenylcarbamoyl]-2-thiobarbituric acid, 1,3-dimethyl-5-[4-(6-trifluoromethylpyrimidin-4-yloxy)phenylcarbamoyl]barbituric acid, 1,3-dimethyl-5-[4-(4-trifluoromethylpyrimidin-2-yloxy)phenylcarbamoyl]barbituric acid, 1,3-dimethyl-5-[4-(2-trifluoromethylpyrimidin-4-yloxy)phenylcarbamoyl]-2-thiobarbituric acid, 1,3-dimethyl-5-[4-methoxy-3-(6-trifluoromethylpyrimidin-4-yloxy)phenylcarbamoyl]-2-thiobarbituric acid, 1,3-dimethyl-5-[3-methoxy-4-(4-trifluoromethylpyrimidin-2-yloxy)phenylcarbamoyl]-2-thiobarbituric acid, 1,3-dimethyl-5-[2-isopropyl-4-(6-trifluoromethylpyrimidin-4-yloxy)phenylcarbamoyl]barbituric acid, 1,3-dimethyl-5-[2,6-dimethyl-4-(2-trifluoromethylpyrimidin-4-yloxy)phenylcarbamoyl]barbituric acid, 1,3-dimethyl-5-[3-methoxy-4-(2-trifluoromethylpyrimidin-4-yloxy)phenylcarbamoyl]barbituric acid, 1,3-dimethyl-5-[4-(2-methyl-6-trifluoromethylpyrimidin-4-yloxy)phenylcarbamoyl]barbituric acid, 1,3-dimethyl-5-[2-isopropyl-4-(6-trifluoromethylpyrimidin-4-yloxy)phenylcarbamoyl]-2-thiobarbituric acid, 1,3-dimethyl-5-[2,6-dimethyl-4-(2-trifluoromethylpyrimidin-4-yloxy)phenylcarbamoyl]-2-thiobarbituric acid, 1,3-dimethyl-5-[4-(5-chloropyrimidin-2-yloxy)phenylcarbamoyl]barbituric acid, 1,3-dimethyl-5-[3-methoxy-4-(5-methyl-4-trifluoromethylpyrimidin-2-yloxy)phenylcarbamoyl]barbituric acid, 1,3-dimethyl-5-[4-(5-phenyl-4-trifluoromethylpyrimidin-2-yloxy)phenylcarbamoyl]barbituric acid, 1,3-dimethyl-5-[4-(4-methyl-6-trifluoromethylpyrimidin-2-yloxy)phenylcarbamoyl]barbituric acid, 1,3-dimethyl-5-[4-(4-methyl-6-trifluoromethylpyrimidin-2-yloxy)phenylcarbamoyl]-2-thiobarbituric acid, 1,3-dimethyl-5-[4-(6-methyl-2-trifluoromethylpyrimidin-4-yloxy)phenylcarbamoyl]barbituric acid and 1,3-dimethyl-5-[4-(2-trifluoromethylpyrimidin-4-yloxy)phenylcarbamoyl]barbituric acid.

12. A compound of formula VII

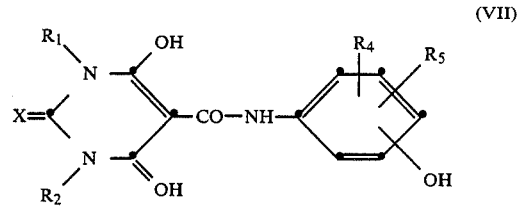

(VII)

wherein $R_1$ is $C_1$-$C_4$alkyl, $C_1$-$C_3$alkoxy, allyl or $C_3$-$C_6$cycloalkyl, $R_2$ is $C_1$-$C_4$alkyl or allyl, $R_4$ and $R_5$ are each independently of the other hydrogen, $C_1$-$C_4$alkyl, $C_1$-$C_4$alkoxy or $C_1$-$C_3$haloalkyl and X is an oxygen or sulfur atom, or of a tautomer or salt thereof said salt being non-toxic to the target host.

13. An anthelmintic composition which has, as active ingredient, at least one compound according to claim 1, or a tautomer or salt thereof, in an amount effective to contain helminths, together with carriers and further adjuvants.

14. A composition according to claim 13, which has 0.1 to 99.0% by weight of a compound of formula I and 99.9% to 1% by weight of further adjuvants.

15. A method of controlling parasitic helminths, which method comprises administering to an animal or anthelmintically effective amount of a compound of formula I according to claim 1.

* * * * *